United States Patent [19]
Weikel

[11] 3,954,457
[45] May 4, 1976

[54] DENTAL AMALGAM
[76] Inventor: Gary Maurice Weikel, 1050 Greenfield Drive, El Cajon, Calif. 92021
[22] Filed: Apr. 28, 1975
[21] Appl. No.: 572,567

[52] U.S. Cl. ................................ 75/169; 75/173 C
[51] Int. Cl.² .......................................... C22C 7/00
[58] Field of Search .............. 75/173 R, 173 C, 169

[56] References Cited
UNITED STATES PATENTS

| | | | |
|---|---|---|---|
| 2,281,991 | 5/1942 | Poetschke | 75/173 C |
| 3,305,356 | 2/1967 | Youdelis | 75/173 C X |
| 3,554,738 | 1/1971 | Beldham | 75/173 C X |
| 3,591,370 | 7/1971 | Denereaz | 75/169 |
| 3,676,112 | 7/1972 | Muhler | 75/173 R |
| 3,841,860 | 10/1974 | Wolf | 75/173 C X |
| 3,871,876 | 3/1975 | Asgar | 75/169 |
| 3,901,693 | 8/1975 | Wolf | 75/169 |

*Primary Examiner*—L. Dewayne Rutledge
*Assistant Examiner*—E. L. Weise
*Attorney, Agent, or Firm*—Lawrence I. Field

[57] ABSTRACT

The addition of copper or copper-base alloys to conventional dental alloys used in amalgams (prior to the formation of the amalgam) has been found to remove tin from its normal matrix phase whereby a more corrosion resistant and clinically improved dental amalgam results.

5 Claims, No Drawings

DENTAL AMALGAM

This invention relates to a clinically improved dental amalgam.

More particularly it relates to a dental amalgam wherein intra-oral corrosion is virtually eliminated by provision of a suitable amalgam composition.

The suitability of alloys of silver with tin for use in dental amalgams has been known for at least 100 years as evidenced by U.S. Pat. No. 157,140, issued Nov. 24, 1874.

Among the improvements which have been made to the Ag-Sn alloy, have been the addition of small amounts of copper, usually not more than 6% by weight and zinc up to 2% by weight, e.g., as described in the Journal of the American Dental association, April 1934 on page 660. The physical properties of dental amalgam alloys are discussed in U.S. Pat. No. 2,281,991 issued May 5, 1942 and in an article in the Journal of the American Dental Association April 1929, page 591.

Further recent United States Patents in this field include:

Youdelis U.S. Pat. No. 3,305,356 issued Feb. 21, 1967
Wolf U.S. Pat. No. 3,841,860 issued Oct. 15, 1974
Beldham U.S. Pat. No. 3,554,738 issued Jan. 12, 1971.

The patent to Youdelis describes the addition of a substantially non-amalgamatable silver base alloy to the known silver-tin-copper-zinc alloy and mercury.

The patent to Wolf describes the use of a mixture of two silver base alloys of silver-copper and tin, one of which is richer in copper.

The patent to Beldham et al describes the addition of gallium to the otherwise known Ag-Sn-Cu-Zn alloy.

The present invention is directed to an improvement over the above noted prior art.

It is known that when the conventional Ag-Sn-Cu-Zn (65:29:6:2) alloy is amalgamated with the mercury prior to its insertion into the teeth, it reacts according to the equation $Ag_3Sn + H_g = Ag_3Sn + Ag_2Hg_3 + Sn_{7-8}Hg$, i.e., some of the $Ag_3Sn$ remains unaffected, and some is decomposed to form silver-mercury and tin-mercury which act as a matrix to bind the AgSn particles.

Intra-oral corrosion of dental amalgams has been extensively investigated. It has been found that the silver-mecury phase ($Ag_2Hg_3$) is more noble than the tin-mercury phase ($Sn_{7-8}Hg$) and that preferential corrosive attack, in oral fluids, takes place in or on the tin-mercury phase, (see Wolf above).

It has been found that clinical deterioration of amalgam is related to the amount of tin-mercury phase present and that an improved dental amalgam results when the tin is present in a more corrosion-resistant matrix form.

Although initial mechanical properties of the amalgam, i.e., strength, hardness and flow, may be improved by the elimination of the mechanically weaker tin-mercury phase, the primary improvement is one of a more corrosion resistant amalgam which ultimately resists mechanical weakness by virtue of its prevailing intact structure.

It has been found that copper, either in elemental form or as a suitable alloy, may be blended with a conventional dental alloy, prior to amalgamation, in proportions of from 0.1 to 25%, preferably 7–10%, to remove tin from its normal matrix phase and cause it to combine with the additive to produce a more corrosion-resistant amalgam. The copper or copper alloy must be in a form which can combine with the tin, whereby the reaction depicted above becomes $Ag_3Sn + [Cu] + Hg \rightarrow Ag_3Sn + Ag_2Hg_3 + Cu_6Sn_5$.

The preferred vehicle for adding the copper to the dental amalgam are alloys of copper and silver containing more than 50% copper, an alloy of 54% Cu—46% Ag being particularly preferred.

The additive, in varying proportions, may be utilized as lathe-cut particles or spheroidal particles or in any other configuration. Ideally, for mechanical and manipulative purposes, the additive is a powder in the size range of 1 to 40 microns or even in the range of 0.001 to 40 microns.

The dental amalgam so produced does not corrode readily and consequently resists mechanical deterioration due to masticatory forces. This amalgam also retains its luster and physical properties to a more satisfactory degree.

It is important that dental amalgam retain its normal laboratory properties when these additives are utilized so in order to prove this fact several experimental tests were conducted. The test specimens were fabricated according to American Dental Association Specification Number 1 for dental amalgam.

Table I shows the compressive strength of amalgams to which up to 30% by weight additions of a 46% Ag—54% copper alloy.

Table I

| | Compressive Strength |
|---|---|
| (a) Conventional amalgam | 57,162 psi |
| (b) Conventional amalgam with 30% of Silver-Copper (46:54) | 61,523 psi |
| (c) Conventional amalgam with 20% Silver-Copper (46:54) | 61,646 psi |
| (d) Conventional amalgam with 10% Silver-Copper (46:54) | 62,293 psi |

Table II shows the % of the SnHg phase present when various amounts of copper-silver additive are added to the conventional amalgams, the alloy being 46 Ag plus 54 Cu.

Table II

| % Additive Added | % $Sn_{7-8}Hg$ |
|---|---|
| 0% | 10% |
| 6% | 2% |
| 10% | 1% |
| 20% | .01% |

Table III shows the tensile strengths obtained with various copper-silver additives.

Table III

| Additive | % Addition | Tensile (psi) |
|---|---|---|
| 46% Ag:54% Cu | 28 | 8,100 |
| | 22.7 | 8,150 |
| | 19 | 8,200 |
| | 15 | 8,275 |
| | 11 | 8,550 |
| 25% Ag:75% Cu | 21 | 8,100 |
| | 16.5 | 8,200 |
| | 12.5 | 8,450 |
| | 11 | 8,700 |
| 10% Ag:90% Cu | 15.8 | 8,100 |
| | 12.75 | 8,250 |
| | 11 | 8,450 |

Table III-continued

| Additive | % Addition | Tensile (psi) |
|---|---|---|
| | 9 | 8,700 |

It will be noted that as the amount of the additive is decreased to about 10%, the tensile strength increases. It will also be noted that with additives richer in copper, smaller amounts of the additive are required. Thus, for tensile strengths of about 8,250 psi, 15% of 46:54 alloy, 12.5% of 25:75 alloy and only 11% of a 10:90 alloy are required. Thus, if enhanced tensile strength is the result desired, the relatively richer copper contents are preferred as additives, while if corrosion resistance is desired, the relatively richer silver contents are preferred.

I claim:

1. A dental amalgam consisting essentially of:
   a. a conventional silver base alloy consisting essentially of approximately 65% Ag, 29% Sn, up to 6% Cu and up to 2% Zn;
   b. and mixed with (a) an additive in particle form selected from the group consisting of elemental copper and copper base alloys; and
   c. mercury to form an amalgam with (a).

2. The amalgam of claim 1 wherein the proportions are approximately:
   a. 70 to 99% by weight; and
   b. 1 to 30% by weight; and (a) plus (b) total 100%; and
   c. 100 to 104% by weight of (a) plus (b).

3. The amalgam of claim 1 wherein the copper is in the form of an alloy of copper and silver, in which the content of copper is at least about 54% by weight.

4. The amalgam of claim 3 wherein the alloy consists of about 54% copper and 46% silver.

5. The amalgam of claim 1 wherein the amount of additive (b) is about 10%.

* * * * *